United States Patent [19]

Hayashi et al.

[11] Patent Number: 5,037,527
[45] Date of Patent: Aug. 6, 1991

[54] REFERENCE ELECTRODE AND A MEASURING APPARATUS USING THE SAME

[75] Inventors: Ryuzo Hayashi, Higashiosaka; Kariyone Akio, Kyoto; Yoshio Hashizume, Nishinomiya, all of Japan

[73] Assignee: Kanzaki Paper Mfg. Co., Ltd., Tokyo, Japan

[21] Appl. No.: 235,970

[22] Filed: Aug. 24, 1988

[30] Foreign Application Priority Data

Aug. 28, 1987 [JP] Japan .................. 62-215822
Jun. 7, 1988 [JP] Japan .................. 63-140833

[51] Int. Cl.⁵ .................................. G01N 27/30
[52] U.S. Cl. ........................... 204/435; 204/56.1; 204/94; 204/403
[58] Field of Search ......... 204/12, 403, 435, 416–419, 204/56.1, 94

[56] References Cited

U.S. PATENT DOCUMENTS

| | | | |
|---|---|---|---|
| 3,151,052 | 9/1964 | Arthur et al. | 204/409 |
| 3,705,089 | 12/1972 | Grubb | 204/435 |
| 3,707,455 | 12/1972 | Derr et al. | 204/403 |
| 3,776,819 | 12/1973 | Williams | 204/403 |
| 3,979,274 | 9/1976 | Newman | 204/403 |
| 4,214,968 | 7/1980 | Battaglia et al. | 204/418 |
| 4,263,343 | 4/1981 | Kim | 204/435 |
| 4,547,280 | 10/1985 | Karasawa et al. | 204/403 |

FOREIGN PATENT DOCUMENTS 62-43555 2/1987 Japan .
62-43556 2/1987 Japan .

*Primary Examiner*—T. Tung
*Attorney, Agent, or Firm*—Wenderoth, Lind & Ponack

[57] ABSTRACT

A reference electrode for use in a flow type measuring apparatus incorporating an immobilized enzyme working electrode, wherein a hydrophilic gel layer is provided on a silver chloride containing layer in order to prevent flow-out of silver ions that are likely to adversely affect enzyme activity, so that the silver chloride containing layer goes into contact through the hydrophilic gel layer with an electrolytic solution containing a substance to be measured.

17 Claims, 11 Drawing Sheets

REFERENCE ELECTRODE AND A MEASURING APPARATUS USING THE SAME

BACKGROUND OF THE INVENTION

1. Field of the Invention

The present invention relates to a reference electrode for use in a continuous flow type measuring apparatus incorporating an immobilized enzyme electrode and, more particularly, to a silver/silver chloride reference electrode which eliminates the possibility of enzyme activity being inhibited due to silver ion run off.

In this specification the term "hydrophilic gel" means a water-containing gel which has affinity for water but is insoluble in water, and which allows migration of ions; it includes no hydrophobic gel.

2. Description of the Prior Art

Measuring techniques using enzyme electrodes for measurement of various chemical substances have recently been widely employed in such areas as clinical chemistry and food chemistry, since they provide a combination of the substrate specificity of enzymatic reaction and the characteristic features of electrochemical analysis such as measurement fastness and high measurement sensitivity. Measuring techniques utilizing enzyme electrodes are classified into the following two kinds of methods:

(1) potentiometric method (or a method of measurement through potential difference detection); and (2) amperometric method (or a method of measurement through detection of electrolytic current at controlled potential). In the potentiometric method, it is necessary that the potential of the working electrode to the reference potential generated at the reference electrode must be accurately measured; and in the amperometric method, it is essential that the potential of the working electrode must be accurately maintained.

In order to accomplish such accurate measurement, the potential of the reference electrode, as a reference potential, must be kept stable, and further the reference electrode must meet the following requirements:

(I) that the electrode reaction on the surface of the reference electrode is reversible and is responsive to a particular chemical species in the electrolyte according to the Nernst equation;

(II) that the reference electrode provides the potential of the reversible reaction, that is stable over a long-time and highly reproducible;

(III) that in the amperometric method wherein two electrodes are employed, the potential of the reference electrode is not changeable, at least only to a negligible extent, due to current during the measuring operation (i.e., non-polarizable) and, when there is any potential change due to any slight current flow, the potential quickly reverts to its original level; and (IV) that there is no potential hysteresis with respect to temperature changes.

Silver/silver chloride reference electrodes are known as satisfying these requirements. A silver/silver chloride reference electrode comprises a half cell consisting of a silver electrode covered with a silver chloride containing layer and a chlorine ion-containing internal solution; and the internal solution of the electrode is electrically connected through a suitable liquid junction to an electrolytic solution to be analyzed. The liquid junction must meet the following requirements:

(I) that in view of the fact that, while the flow rate of the internal solution from the reference electrode should not be unreasonably large in order to minimize contamination of the solution to be analyzed by the internal solution, an excessively slow flow of the internal solution may result in the occurrence of an abnormal liquid junction potential. Therefore, the liquid junction should allow a moderate flow of the internal solution;

(II) that in order to obtain a stable and well reproducible liquid junction potential, the flow rate of the internal solution should be constant.

That is, a reference electrode should be such that the internal solution is allowed to flow at a constant rate out of the electrode through the liquid junction.

To this end, micro-pore, salt bridges, fritted glass means, or the like have hitherto been employed as liquid junctions that electrically interconnect the reference electrode and the electrolytic solution for electrolytic measurement.

The miniaturization of a reference electrode makes it possible to reduce the distance between the working electrode and the reference electrode, thereby lowering the degree of possible voltage drop due to solution resistance, so that the potential of the working electrode can be kept more stable, it being thus possible to obtain very accurate measurements. Therefore, attempts have been made to reduce the size of silver/silver chloride reference electrodes; however, the attempts have involved such problems as are discussed below.

The miniaturization of a silver/silver chloride reference electrode along with the reduction of size of a relevant enzyme electrode results in an increased proportion of the internal solution flowing out through the liquid junction in relation to the total amount of the internal solution, which fact possesses a problem with respect to the potential stability of the reference electrode.

Another problem is that when the size of the liquid junction for the silver/silver chloride reference electrode is reduced to slow down the flow of the internal solution through the junction, an abnormal liquid junction potential is likely to occur at the liquid junction.

Further problems are that where salt bridges are employed, it is impracticable to miniaturize the whole of the silver/silver chloride reference electrode including the salt bridges, and that if there is any difference in chlorine ion concentration between the internal solution of the electrode and the solution being measured, it is difficult to obtain good potential stability because the internal solution is liable to change in chlorine ion concentration.

As pointed out above, the prior art silver/silver chloride reference electrodes having an internal solution and a liquid junction can hardly be miniaturized because of their structural configuration; and therefore, the present inventors have considered a concept that a reference electrode having a silver chlorde containing layer provided on silver wires is directly inserted into electrolytic solution for electrolytic measurement.

A silver/silver chloride reference electrode is produced, for example, by the following. A silver electrode is dipped into the electrolytic solution containing chlorine ions. Electric current is flowed between the silver electrode as anode and a platinum electrode by employing, for example, a controlled current generating apparatus, whereby a thin silver/silver chloride layer is formed on the surface of the silver electrode (electroplating method). This method has an advantage that it can easily produce silver/silver chloride electrodes, on the one hand, but on the other hand, it involves disadvantages in that the thin layer formed is not satisfactory in physical strength, and that the thin layer is likely to peel off in the course of prolonged use, it being thus unable to obtain good potential stability.

A reference electrode for an enzyme electrode which is press-molded from a silver/silver chloride/silver sulfide mixture is also known (Japanese Patent Laid Open Publication No. 43556/1987). This reference electrode has the drawback that production of the electrode requires difficult molding work, which fact virtually denies the possibility of such electrode being produced in a miniaturized form.

When, as above described, a silver/silver chloride reference electrode is placed in the electrolytic solution directly and without use of any salt bridge, an enzyme electrode may, depending upon the variety of enzymes used therein, lose their activity very rapidly due to silver ions dissolved slightly from the silver/silver chloride reference electrode.

Silver chloride is slightly soluble in water (1.9 mg/l), and silver ions enter into good combination with proteins. Whilst, certain enzymes may be adversely affected or inactivated by the presence of silver ions. A number of such enzymes are known including, for example, L-sorbose oxidase (E. C. 1, 1, 3, 11), inulinase (E. C. 3, 2, 1, 7), α-D-glucosidase (E.C. 3, 2, 1, 20), β-D-glucosidase (E. C. 3, 2, 1, 21), β-D-galactosidase (E.C. 3, 2, 1, 23), and invertase (E. C. 3, 2, 1, 26).

It has been proposed to employ a palladium electrode as a reference electrode in order to prevent inactivation of enzymes due to silver ions (as in U.S. Pat. No. 4,547,280), but such electrode does not fully satisfy the aforesaid requirements for reference electrodes; it still involves a problem from the view point of long-term potential stability.

It is apparent from what is discussed above that no effective measures have ever been proposed for miniaturization of silver/silver chloride reference electrodes.

SUMMARY OF THE INVENTION

It is a primary object of the invention to provide a silver/silver chloride reference electrode which eliminates the aforesaid problems, and which is free from the possibility of inactivating enzymes and can be produced in a reduced size.

It is another object of the invention to provide a silver/silver chloride reference electrode which has good physical strength, long time serviceability, and high potential stability, and which can be easily produced in reduced size.

These and other objects of the invention will be understood by reference to the following description which is considered in connection with the accompanying drawings.

In order to accomplish the foregoing objects, the invention provides a silver/silver chloride reference electrode comprising a hydrophilic gel layer formed on a silver chloride containing layer, thereby the silver chloride containing layer being in contact with electrolytic solution through the hydrophilic gel layer. Preferably the hydrophilic gel layer has a thickness of 0.1-20 mm.

In a preferred embodiment of the invention, the hydrophilic gel layer is composed of at least one selected from the group consisting of polysacchloride gel, hydrophilic synthetic polymer gel and protein gel.

In another preferred embodiment of the invention, the polysacchloride gel is composed of at least one selected from the group consisting of agarose, agaropectin and κ- carrageenan.

In another preferred embodiment of the invention, the hydrophilic synthetic polymer gel is composed of at least one selected from the group consisting of polyacrylamide and polyvinylalcohol.

In another preferred embodiment of the invention, the protein gel is composed of (a) at least one selected from the group consisting of albumin, globulin and gelatin, and (b) a crosslinking agent, and preferably the protein gel is composed of albumin and the crosslinking agent.

In a preferred embodiment of the invention, the crosslinking agent of the silver/silver chloride reference electrode is an aldehyde.

In a more preferred embodiment of the invention, the aldehyde is composed of at least one selected from the group consisting of formaldehyde, glutaraldehyde and glyoxal.

According to the invention, the silver chloride containing layer is formed by processing a silver electrode electrolytically in the electrolytic solution containing chlorine ions.

In a preferred embodiment of the invention, the silver chloride containing layer is formed by the steps of:

processing a silver electrode electrolytically in an electrolytic solution which contains a protein having an isoelectric point lower than the pH of the electrolytic solution, thereby forming a thin layer, which contains a mixture of silver, silver chloride and protein, and treating the thin layer with a crosslinking agent.

In a more preferred embodiment of the invention, the protein is composed of at least one selected from the group consisting of globulin, ovalbumin, serum albumin, collagen, and gelatin.

In another preferred embodiment of the invention, the crosslinking agent is composed of at least one selected from the group consisting of formaldehyde, glutaraldehyde and glyoxal.

More preferably, the hydrophilic gel layer is composed of at least the protein and the crosslinking agent, and the crosslinking agent of the hydrophilic gel layer is the same as the crosslinking agent using for crosslinking of the silver chloride containing layer.

The invention provides a silver/silver chloride reference electrode which is formed by the steps of:

dissolving a protein having an isoelectric point lower than the pH of electrolytic solution containing chlorine ions in the electrolytic solution, processing a silver electrode electrolytically in the electrolytic solution, thereby forming a thin layer, which contains a mixture of silver, silver chloride and protein, and treating the thin layer with a crosslinking agent.

The invention further provides a measuring apparatus comprising:

(a) a silver/silver chloride reference electrode having:

(a1) a silver chloride containing layer, and (a2) a hydrophilic gel layer formed on the silver chloride containing layer; and (b) an immobilized enzyme working electrode.

In a preferred embodiment of the invention, the measuring apparatus has the immobilized enzyme working electrode comprising an immobilized enzyme which has the characteristic that its activity is inhibited by silver ion, more preferably the enzyme is selected at least one from the group consisting of L - sorbose oxidase, inulinase, α - D - glucosidase, β - D - glucosidase, β - D - galactosidase, invertase and glucoamylase.

In a more preferred embodiment of the invention, the measuring apparatus is a flow type measuring apparatus, comprising a measuring cell having a flow path and for holding the silver/silver chloride reference electrode and the immobilized enzyme working electrode to face the flow path.

BRIEF DESCRIPTION OF THE DRAWINGS

Detailed description of the invention will be made with reference to the accompanying drawings, in which.

DETAILED DESCRIPTION OF THE PREFERRED EMBODIMENTS

The detailed description that will follow represents what is at present considered to be the preferred embodiments of the invention. It is to be understood that the description of the embodiments is only illustrative of the general concept of the invention and not restrictive, since the scope of the invention is defined by the appended claims.

According to the invention, a hydrophilic gel layer 2 is mounted on a silver chloride containing layer 1 of a silver/silver chloride reference electrode 3, whereby the provision of an internal solution and a liquid junction is rendered unnecessary, so that the reference electrode 3 can be produced in a reduced size. The silver chloride containing layer 1 goes in contact with an electrolytic solution through the hydrophilic gel layer 2, and thus the leakage of silver ions can be prevented, which means that enzyme activity in an immobilized enzyme working electrode 5 are not liable to be inhibited. Therefore, prolonged stable measurement can be assured.

Figure 1:
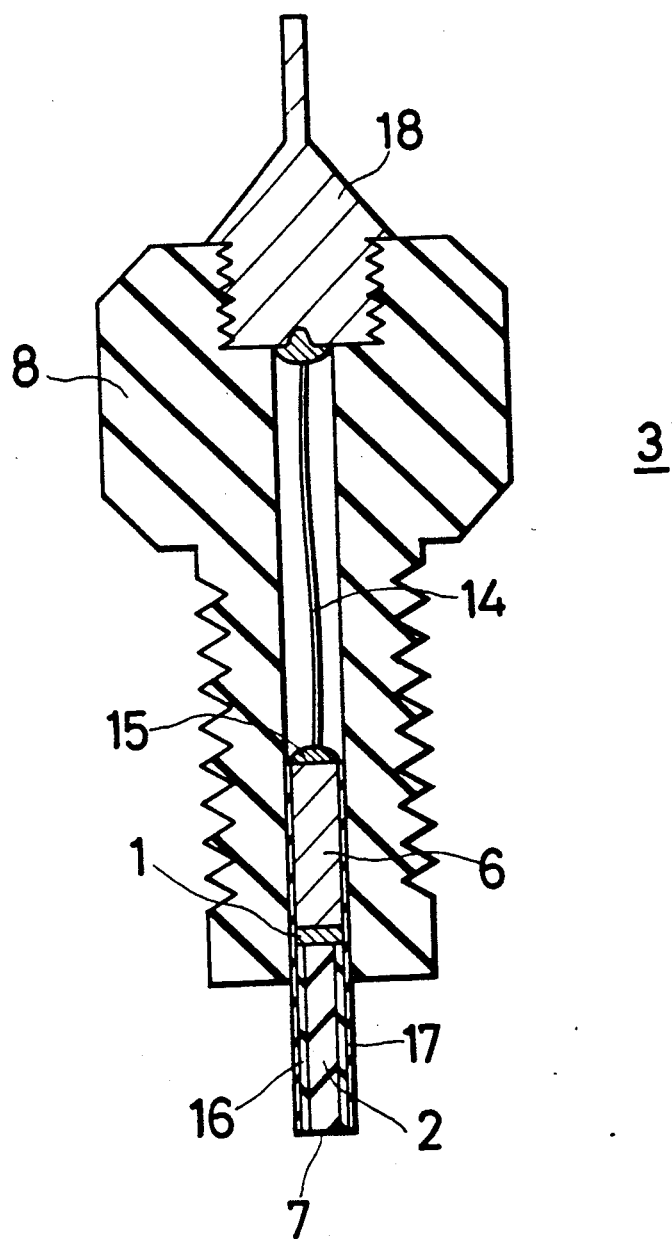
FIG. 1 is a sectional view showing a silver/silver chloride reference electrode 3 which represents one embodiment of the invention.

Referring to FIG. 1, the procedure for production of the reference electrode 3 according to the invention will now be described in detail, in which, by way of example, description relates to the case where a silver/silver chloride containing layer is formed by the electroplating technique. A silver wire element 6 is thoroughly abraded so that an oxide layer present on its surface is removed. A silver lead wire 14 is connected to one end of the silver wire element 6 by using a conductive adhesive 15. One end of a tubular member 16 formed of an electrically insulative material, such as acrylic resin, is held in abutment with or disposed in spaced apart relation with the other end of the silver wire element 6. The silver wire element 6 and the tubular member 16 are covered with a film-like tubular member 17 formed of a heat-shrinkable Teflon or the like material, being held together in such condition that they are linearly coaxially connected.

The silver wire element 6 is then dipped in an electrolytic solution containing chlorine ions, e.g., an aqueous solution of chloride, or a buffer solution having a chloride dissolved therein. For the purpose of the buffer solution, various kinds of such solution may be used including, for example, phosphoric acid and citric acid buffer solutions. For the purpose of the electrolytic solution, an aqueous solution of hydrochloric acid or an aqueous solution of alkali metal chloride, such as sodium chloride or potassium chloride can be used. The concentration of such chloride should be 0.01–1M.

Then, with a platinum wire as a counter electrode and the silver wire element 6 as a silver electrode (as anode), electrolytic process is carried out with respect to a saturated calomel electrode (hereinafter referred to as SCE).

The potential for electrolysis is not lower than +0.05 V relative to SCE, and a sufficient amount of silver chloride can be formed by increasing the potential to +0.20 V relative to SCE. Time required for electrolysis is usually within the range of 1 to 480 minutes, preferably 5 to 60 minutes.

In this connection it is advisable to form a layer containing silver chloride and protein by mixing a protein, such as bovine serum albumin, into the electrolytic solution. Then the protein is gelatinized using crosslinking agent. This provides an advantage that increased inter-layer bond can be obtained in the case of using the same protein gel as is used for the hydrophilic gel layer 2. This point will be described hereinafter in further detail.

Hydrophilic gel is then filled into a space between a contact portion to the electrolytic solution 7 and the silver chloride containing layer 1 thus formed on the silver wire element 6.

The silver wire element 6, silver chloride containing layer 1, the tubular members 16 and 17, and the hydrophilic gel layer 2 are integrally fixed to a supporting body 8. The supporting body 8 is formed of electrically insulative materials, such as fluoric synthetic resin and vinyl chloride. The silver lead wire 14 is connected to a connector 18 by a conductive adhesive. The connector 18 is secured to the supporting body 8.

Gel filling may be performed by filling a separately prepared gel into the space between the silver chloride containing layer 1 and the contact portion 7, or by filling a protein/crosslinking agent solution, for example, into the space, then gelatinizing the solution.

Examples of hydrophilic gel useful for this filling purpose may be mentioned; polysaccharide gels, such as agarose, agaropectin, and κ-carrageenan: hydrophilic synthetic polymer gels, such as polyacrylamide gel, and polyvinylalcohol gel; and protein gels, such as albumin, globulin, and gelatin.

To prepare polysaccharide gel, such as agarose gel, a hot aqueous agarose solution having a concentration of the order of 1-10%, which contains crosslinking agents, such as diisocyanate and boric acid, is cooled to room temperature.

To prepare polyacrylamide gel, crosslinking agents, such as N, N'-methylene bis-acrylamide, and polymerization promoters, such as peroxo ammonium disulfate, and N, N, N', N'-tetramethylethylenediamine, are added into an acrylamide solution, and the mixture is allowed to gelatinate. The resulting gel is preserved in water or in a buffer solution, being thereby desalted.

To prepare polyvinylalcohol gel: aldehydes, such as glutaraldehyde; a methylol compound, such as N-methylol melamine; an activated vinyl compound, such as divinylsulfone; an epoxy compound, such as epichlorohydrin; or an inorganic crosslinking agent, such as dicarboxylic acid, diisocyanate or copper salt, is added to polyvinyl alcohol for gelatinization: or in the presence of hot water or water the polyvinyl alcohol is subjected to crosslinking reaction by electron beam irradiation or UV light irradiation, being thereby gelatinized.

To gelatinize protein through its reaction with a crosslinking agent, various known crosslinking agents for proteins may be used. Above all, aldehydes such as formaldehyde, glutaraldehyde, and glyoxal, are preferred, since they are highly water soluble and can provide good physical strength.

For the purpose of protein gelatinization by using the crosslinking agent, the concentration of the protein is preferably 0.1 to 10 wt % and the concentration of the crosslinking agent is preferably 0.1 to 10 wt %. If the protein concentration is less than 0.1 wt %, no sufficient gel strength is obtainable and the resulting gel layer is likely to peel off. If the protein concentration is more than 10 wt %, the resulting solution is excessively viscous and difficult to operate. If the concentration of the crosslinking agent is less than 0.1 wt %, the gel strength is insufficient, and if it is more than 10 wt %, reaction occurs too fast and no uniform gelation is obtainable.

Gelation may be allowed to take place at room temperature, or may be employed to take place under heating or cooling conditions. For the purpose of crosslinking with aldehydes, it is advisable to carry out crosslinking in a sealed vessel and under a saturated vapor atmosphere of aldehyde solution, because uniform crosslinking gel is obtainable.

Among various kinds of hydrophilic gel, protein gel in particular can be advantageously used, since mercapto groups in the protein take in silver ions to produce mercaptide and thus dissolution of silver ions can be effectively prevented. More particularly, protein substances, such as albumin, which contain a larger proportion of mercapto groups, are preferably used.

The thickness of the hydrophilic gel is 0.1 mm-20 mm, preferably 0.5 mm-10 mm. If the thickness is less than 0.1 mm, the gel layer is likely to peel off under a shear force. If the thickness is more than 20 mm, the electrode is necessarily greater in size and the distance of ion diffusion is larger, with the result that the potential is unstable.

Figure 2:
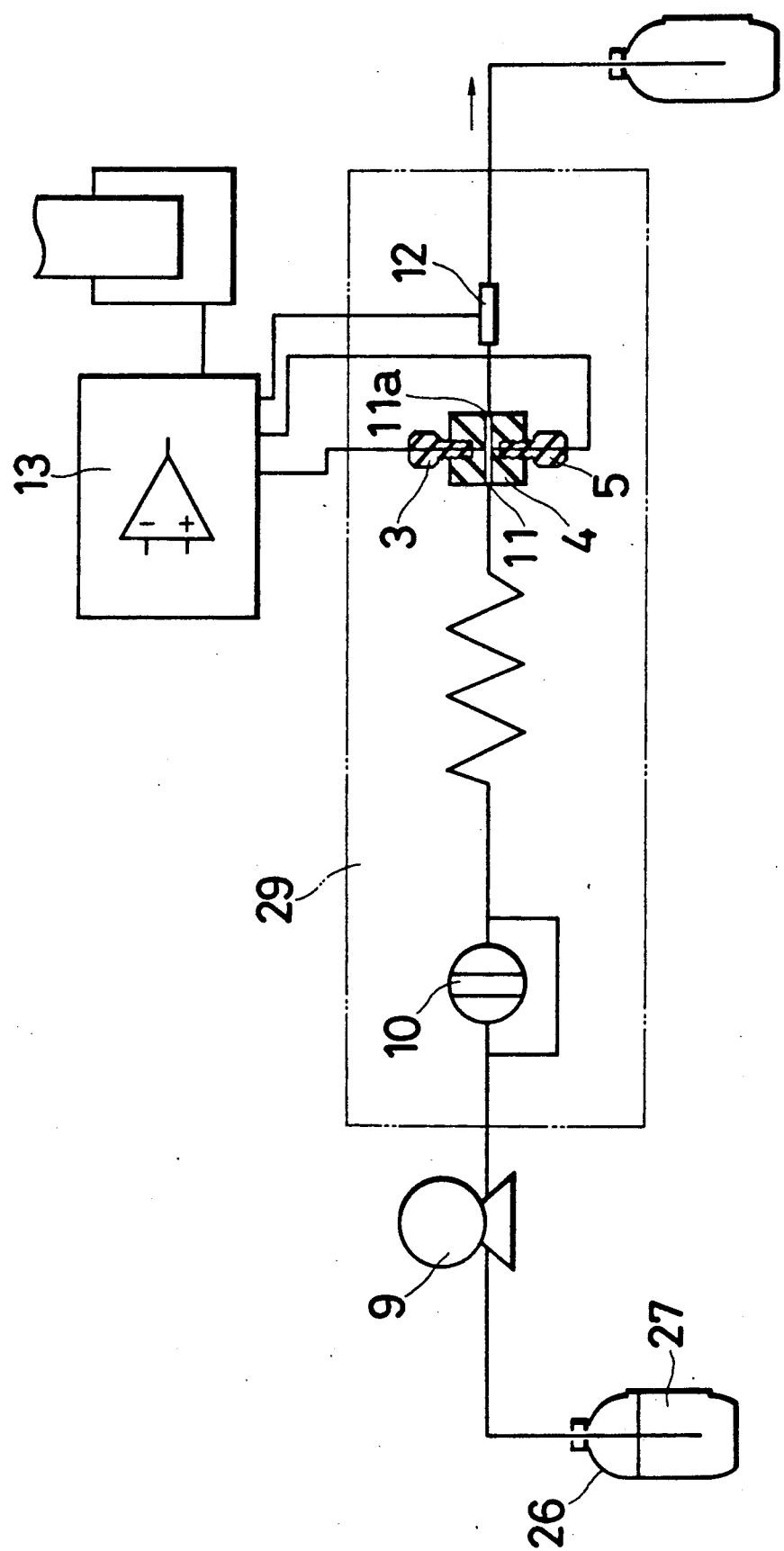
FIG. 2 is a system diagram showing a flow type measuring apparatus embodying the invention.

The silver/silver chloride reference electrode 3 thus produced has no internal solution, nor has it a liquid junction structure. Therefore, it can be produced in reduced size. Furthermore, the hydrophilic gel layer 2 has good physical strength characteristics. When the reference electrode 3 is employed in a flow type measuring apparatus (to be hereinafter described; FIG. 2), the electrode 3 is exposed to shearing force of a buffer solution. But for above mentioned reason, no such problem as potential change due to flow out of internal solution is caused, even if the reference electrode 3 is disposed in opposed relation of the immobilized enzyme working electrode 5 (a platinum electrode or the like on the surface of which an enzyme is immobilized) and held in direct contact with a stream of buffer solution.

FIG. 2 is a system diagram showing a flow type measuring apparatus equipped with the reference electrode 3 as shown in FIG. 1. A buffer solution (electrolytic solution) 27 in a vessel 26 is supplied at constant flow rate by means of a pump 9. A sample solution to be measured is supplied from an injector 10 of a thermostat 29 for mixing with the buffer solution (electrolytic solution). A measuring cell 4 is connected to a pipe leading to the injector 10 by a pipe joint 11, and is also connected to a pipe leading to an auxiliary electrode or counter electrode 12 by a pipe joint 11a. The silver/silver chloride reference electrode 3 according to the invention is mounted in the measuring cell 4. An immobilized enzyme working electrode 5 is also mounted in the cell 4. Value of output current from this working electrode 5 is measured by a potentiostat 13.

Figure 3A:
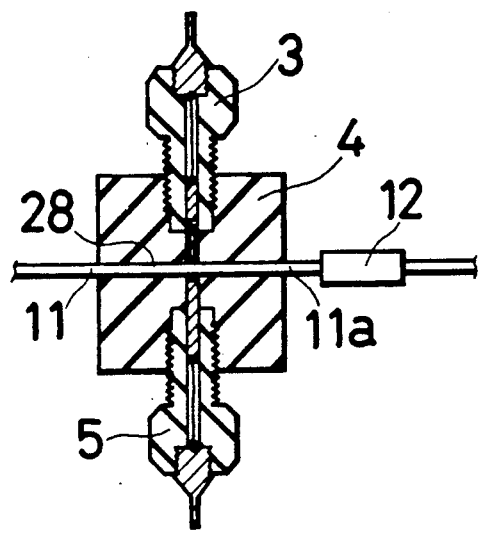
FIGS. 3a, 3b, and 3c are respectively sectional views showing three different forms of measuring cells according to the concept of the invention.

FIG. 3a is an enlarged sectional view of the measuring cell 4. The electrodes 3 and 5 are disposed in opposed relation in a flow path, so that the distance between them is smaller than that in the prior art arrangement, whereby measurement accuracy can be improved.

Figure 3B:
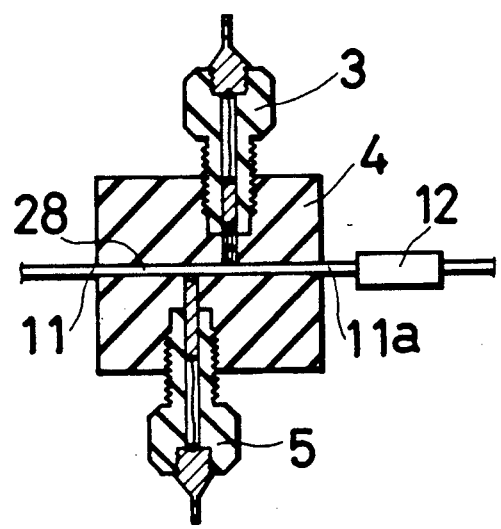

FIG. 3b is a sectional view showing another form of measuring cell 4 according to the invention. The electrodes 3, 5 are disposed in generally opposed but slightly catercornered relation across the flow path 28.

Figure 3C:
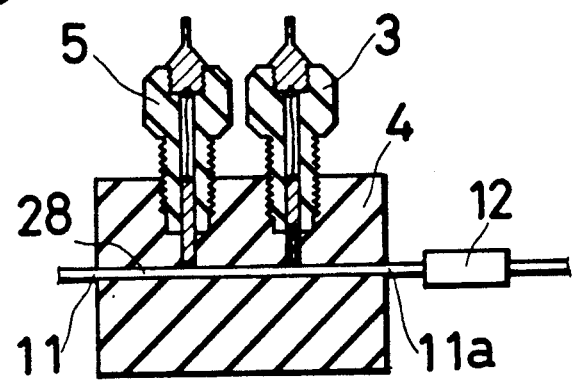

FIG. 3c is a sectional view showing still another form of measuring cell 4 according to the invention. The electrodes 3 and 5 are slightly spaced apart along the flow path 28 on one side thereof (at the upper side in FIG. 3c).

Figure 4:
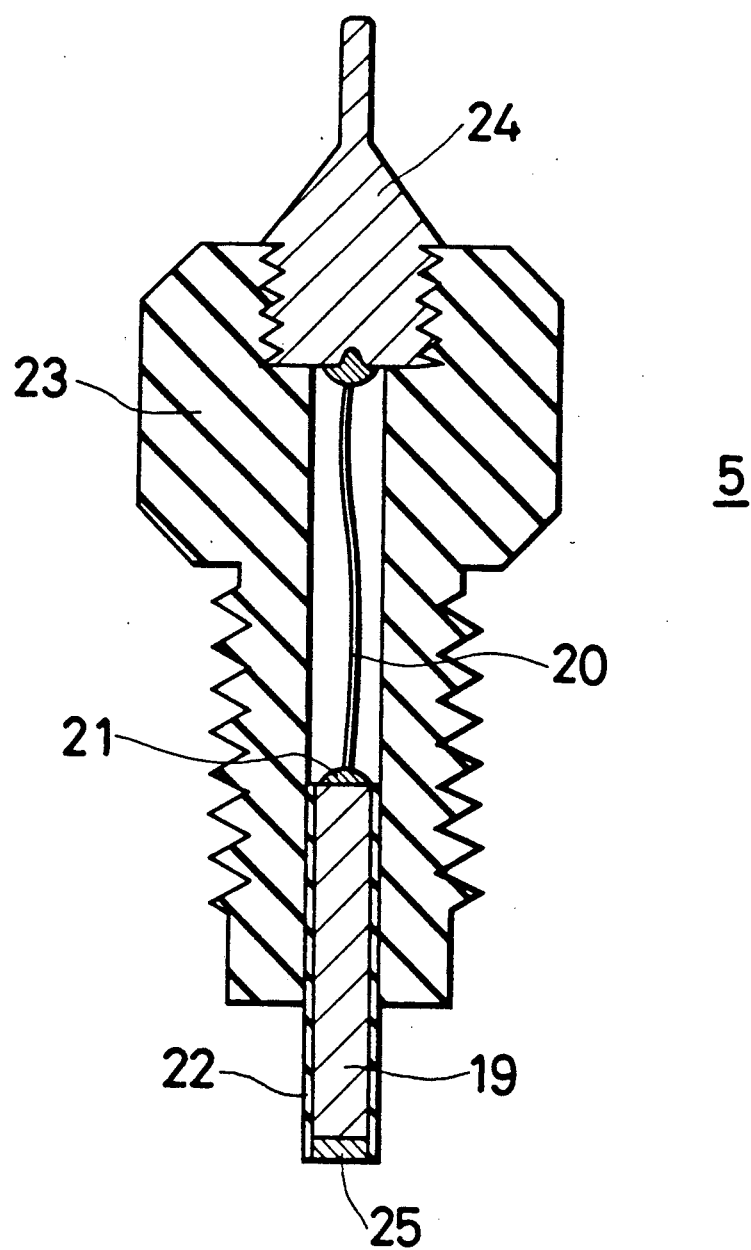
FIG. 4 is a sectional view showing an immobilized enzyme working electrode employed in conjunction with the reference electrode 3 according to the invention.

FIG. 4 is a sectional view showing an immobilized enzyme working electrode 5. A silver lead wire 20 is connected by means of a conductive adhesive 21 to a platinum wire element 19 which has been abraded. The platinum wire element 19 is covered with an electrically insulative film-like tubular member 22 formed of a heat shrinkable Teflon material, and is fixed to a supporting body 23. The supporting body 23 is formed of an electrically insulative material, such as fluoric synthetic resin, and a vinyl chloride material or the like. The lead wire 0 is connected to a connector 24 through a conductive adhesive. The connector 24 is fixed to the supporting body 23. An immobilized enzyme layer 25 is formed at one end of the platinum wire element 19.

In this connection, potassium chloride or the like is added within the range of 0.01–0.5M to the buffer solution used in the flow type apparatus so that the buffer solution contains chlorine ions. As a result, the potential of the reference electrode 3 is further stabilized and thus high accuracy measurement is made possible.

The reference electrode of the invention eliminates the possibility of flow out of silver ions. Therefore, even if the reference electrode is disposed adjacent the immobilized enzyme working electrode on which enzyme that is liable to be adversely affected by silver ions, such as invertase, the immobilized enzyme is not likely to be inactivated. Hence, high accuracy measurement is possible by the reference electrode being disposed adjacent the immobilized enzyme working electrode.

According to the invention, a hydrophilic gel is preferably introduced into the silver chloride containing layer 1, and thereafter a hydrophilic gel layer 2 is formed on the silver chloride containing layer 1. Thus, it is possible to produce a reference electrode having such longer serviceability and more stable and reliable measurement performance. In this case, employing a crosslinked protein as the hydrophilic gel, which is contained in silver chloride containing layer 1, is preferred because excellent performance characteristics can be obtained and the silver chloride and protein containing layer can be easily prepared. The protein itself has a negative charge at a pH value above its isoelectric point, and therefore it can be electrodeposited simultaneously upon formation of an AgCl containing layer. Thus, it is quite easy to prepare such layer.

When a silver chloride containing layer is electrochemically formed by the electroplating technique, a protein having an isoelectric point lower than the pH of an electrolytic solution containing chlorine ions (i.e., protein having a negative charge in the electrolytic solution) is put into the electrolytic solution.

The protein having a negative charge is allowed to migrate to and be adsorbed onto the surface of a silver electrode, i.e., anode. As a consequence, a thin layer of silver, silver chloride and protein mixture is formed; and by subjecting the protein in the thin layer with a crosslinking agent there is formed a thin layer having excellent physical strength characteristics.

A hydrophilic gel layer 2 is formed on the silver/silver chloride reference electrode thus obtained, as in FIG. 1. According to such arrangement, the silver/silver chloride thin layer provides high strength characteristics, and a high degree of affinity is present between the silver chloride containing layer 1 and the hydrophilic gel layer 2; and further there is no clearance between the two layers 1 and 2. Therefore, the reference electrode can provide stable potential for much more long period of time.

The arrangement of the silver/silver chloride reference electrode 31 will now be described in further detail. A silver wire element is first throughly abraded, and an oxide layer is removed. Then, an electrolytic solution is prepared which comprises an aqueous solution of chloride or a buffer solution having chloride dissolved therein, and a protein introduced into such solution; and the silver wire element is dipped into the electrolytic solution. Various kinds of buffer solutions may be used, but in view of the fact that isoelectric points of many protein substances are present in a weak acid zone, a phosphoric acid buffer solution is advantageously used. In order to maintain the protein solution in a stable condition, the concentration of the buffer solution should be of the order of 0.01–1M, preferably 0.05–0.5M.

For the chloride, hydrochloric acid may be used, but alkali metal chlorides, such as sodium chloride and potassium chloride, are preferably used because they are not likely to cause gelation or precipitation of proteins. The concentration of the chloride should be of the order of 0.01–1M.

Various proteins having an isoelectric point lower than the pH of the buffer solution are used in the practice of the invention, but inter alia globulin (pI 6.4–7.2), ovalbumin (pI 4.6), serum albumin (pI 4.8), collagen, and gelatin are preferably used because they help to obtain a high strength crosslinked protein layer. Protein concentration should be within the range of 0.1–100 mg/ml, preferably 0.5–50 mg/ml, in order to avoid electrolyte bubbling and to produce a crosslinked layer having sufficient strength.

Nextly, electrolysis is carried out with respect to a saturated calomel electrode (hereinafter referred to as SCE) by using platinum as a counter electrode and a silver electrode as anode.

The potential for electrolysis should be not lower than +0.05 V relative to SCE. Sufficient protein adsorption can be effected by increasing the potential to +0.2 V relative to SCE. Time required for electrolysis should be 1–480 minutes, preferably 5–60 minutes. If the time is too short, no sufficient layer strength is obtainable, whereas if the time is excessively long, the resulting layer is too thick, which may be a cause of cracking in a finally formed crosslinked layer.

Subsequently, the thin silver/silver chloride/protein layer thus formed on the silver wire element is treated with a crosslinking agent. For the crosslinking agent, various known crosslinking agents for proteins may be used, but inter alia aldehydes, such as formaldehyde glutaraldehyde, and glyoxal, are preferably used because they are highly water soluble and can provide sufficient physical strength. Crosslinking treatment is given after the completion of the electrolytic process and in the following manner. The electrode, lightly washed in water, is dipped in a 0.1–10% aqueous solution of the crosslinking agent, then dried and cured; or the crosslinking agent may be previously included in the electrolytic solution. In the latter case, however, it is necessary that the protein and the crosslinking agent should be of low concentration in order to avoid gelation of the electrolyte during electrolytic process.

It is also possible to effect heating at temperatures of 40°–60° C. to accelerate curing reaction.

Figure 5:
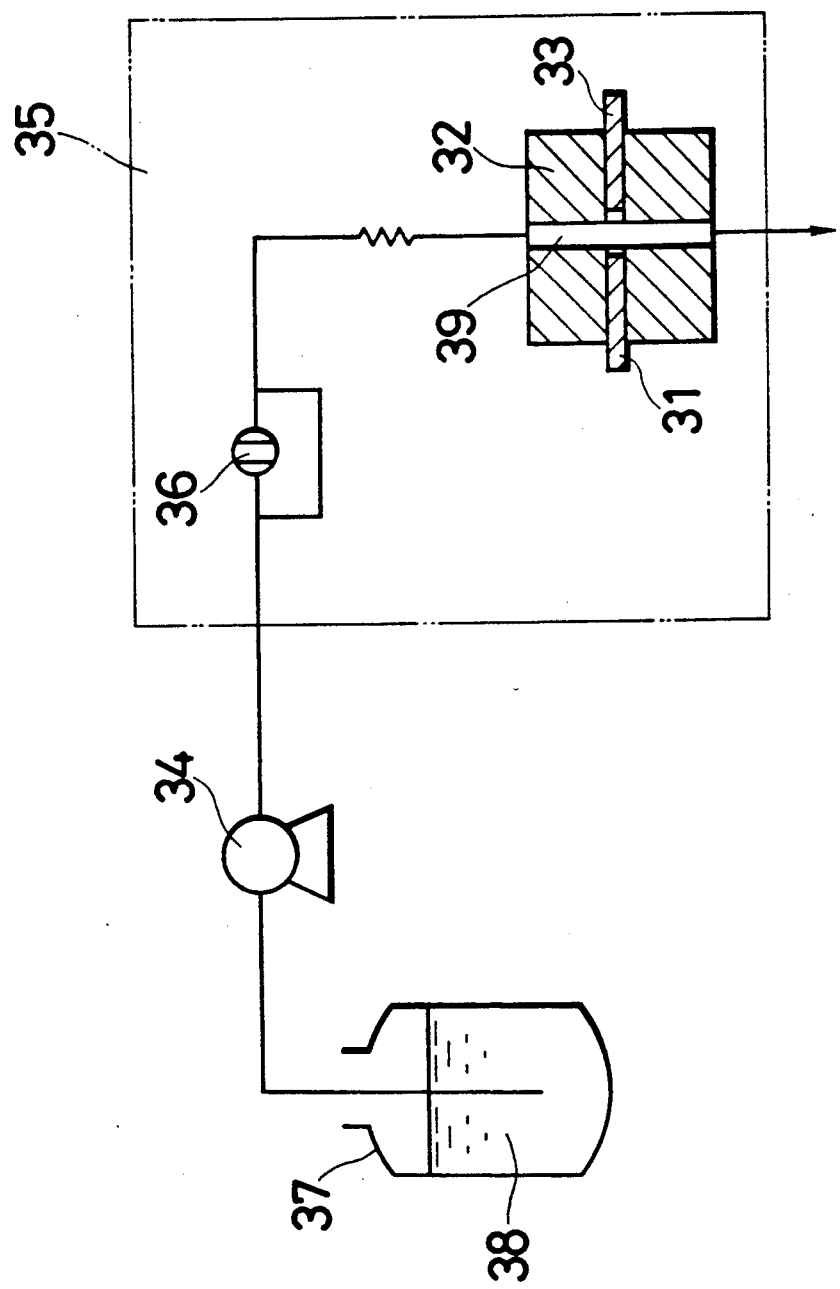
FIG. 5 is a system diagram showing another form of flow type measuring apparatus embodying the invention.

The reference electrode obtained by the above mentioned operation is applied to, for example a measuring apparatus shown in FIG. 5.

FIG. 5 is a system diagram showing a flow type measuring apparatus which represents another embodiment of the invention. A buffer solution (electrolytic solution) 38 in a vessel 37 is supplied at constant flow rate by means of a pump 34. A measuring substance is injected from an injector 36 of a thermostat 35. A reference electrode 31, of which the silver chloride containing layer contains the protein and is crosslinked according to the invention, and an enzyme working electrode 33 are mounted on a flow path 39 in a measuring cell 32.

The reference electrode 31 thus obtained can be used as it is, but it is preferable to prevent possible dissolution of silver ions, by forming a hydrophilic gel layer 2 in the manner as earlier described with reference to FIG. 1. The crosslinking agent used in this connection is preferably the same as the one used in the formation of the silver chloride containing layer 1. The reason is that where the crosslinking agent used for the hydrophilic gel layer 2 is different from the one used for the silver chloride containing layer 1, the crosslinking and curing treatment may involve different shrinkage factors, which is likely to result in gel separation.

In the case of using the silver/silver chloride reference electrode 31, on which no hydrophilic gel layer is formed, the silver/silver chloride reference electrode 31 may be immersed into a potassium chloride solution of a given concentration in a glass tube or the like, the assembly can be employed through a suitable liquid junction as a reference electrode. It is also possible to arrange that the reference electrode is encapsulated in a cylindrical vessel together with a working electrode, the surface of which vessel is covered with a permselective membrane, such as an acetyl cellulose membrane, so that the assembly can be used as an enzyme electrode.

Further, the reference electrode of the invention can be employed in a flow type enzyme electrode measuring apparatus, in which a shear force of a buffer solution is present, in such manner that, as FIG. 5 shows, the reference electrode is disposed in opposed or parallel relation to a working electrode 33 (a platinum electrode or the like on the surface of which an enzyme is immobilized) so that the surface of its silver/silver chloride layer is in direct contact with a stream of the buffer solution. Even in such case, the reference electrode is allowed to operate prolonged stable measurement since its thin silver/silver chloride layer has sufficient physical strength characteristics. In this connection, it is desirable that the buffer solution used in the flow type measuring apparatus is loaded with potassium chloride within the range of 0.01–0.5M so that it contains chlorine ions, whereby the potential of the reference electrode 31 is further stabilized and far more accurate measurement can be assured. In the case of the reference electrode being directly contact with a stream of the buffer solution, no liquid junction is required and accordingly it is possible to miniaturize the measuring cell 32 for housing the enzyme electrode 33.

Following examples are given to illustrate the invention in further detail; it is to be understood, however, that the invention is not limited to the examples In the examples, the unit showing "%" represents weight percentage.

EXAMPLE 1

Explanation is given with reference to FIG. 1 Ends of a 2 mm dia., 5 mm long silver wire element 6 were finished flat with 1600-mesh emery paper, and a 0.1 mm dia., 20 mm long silver lead wire 14 was bonded to one end of the silver wire element 6 with a thermosetting conductive adhesive 15, which was subjected to heat curing treatment in an electric oven at 120° C. for one hour. The other end of the silver wire element 6 was brought in contact with one end of an acrylic tubular member 16 having an outer diameter of 2 mm, an inner diameter of 1 mm, and a length of 5 mm so that the wire element 6 and the tubular member 16 were aligned straight, and the outer periphery of the assembly was covered with a heat shrinkable Teflon made tubular member 17.

The front end portion of the assembly was immersed in a buffer solution of 0.1M sodium phosphate containing 0.05M potassium chloride at pH 7.0, which was employed as a working electrode, with a 1 cm square platinum electrode as a counter electrode and SCE as a reference electrode. Electrolysis was carried out at +0.2 V for 30 minutes at room temperature, and a silver chloride containing layer 1 was thus formed.

After the end of the electrolytic process, the silver wire was lightly washed in water, and an aqueous solution of 5.0% bovine serum albumin containing 5.0% glutaraldehyde was filled by a microsyringe into the space within the acrylic tubular member 16. Then, the assembly was allowed to incubate 30 minutes at room temperature for gelation. A hydrophilic gel layer 2 was thus formed.

The silver wire element 6 was fixed to a supporting body 8 and a plug type connector 18 having a silver lead wire soldered thereto was mounted in position. A silver/silver chloride reference electrode was thus obtained.

Nextly, a working electrode 5 will be described with reference to FIG. 4. Ends of a 2 mm dia., 10 mm long platinum wire 19 were finished flat with 1600-mesh emery paper, and a 0.1 mm dia., 20 mm long silver lead wire 20 was bonded to one end of the platinum wire 19 with a thermosetting conductive adhesive 21, which was heated in an electric oven at 120° C. for curing treatment for 1 hour. The outer periphery of the platinum wire was covered with a heat shrinkable Teflon-made tubular member 22, and the so covered platinum wire was fixed to an electrode supporting body 23. A plug type connector 24 having a silver lead wire 20 soldered thereto was mounted to the supporting body 23. The platinum wire 19 was provided at one end thereof with an immobilized enzyme membrane 25 having a combination of glucose oxidase, invertase, and mutarotase immobilized thereto, together with bovine serum albumin, by glutaraldehyde. The working electrode 5 was thus obtained.

The silver/silver chloride reference electrode 3 and the working electrode 5 were mounted in the measuring cell 4 shown in FIG. 3a, and a pipe connector having electric conductivity was disposed on a pipeline connected to the measuring cell 4 and at the downstream side thereof, which connector was made to serve as an auxiliary electrode (counter electrode) 12.

This three-electrodes measuring cell was connected to the pipeline and incorporated into the flow type measuring apparatus in FIG. 2. A predetermined voltage was applied by a potentiostat 13 and measurement was made by recording output current values by means of a recorder.

A buffer solution of 0.1M sodium phosphate at pH 7.0, including 0.05M potassium chloride, was supplied at the flow rate of 1.0 ml/min by means of a pump 9. The following measurements were carried out in a thermostat 29 (inner temperature of 37.0±0.2° C.).

Figure 6:
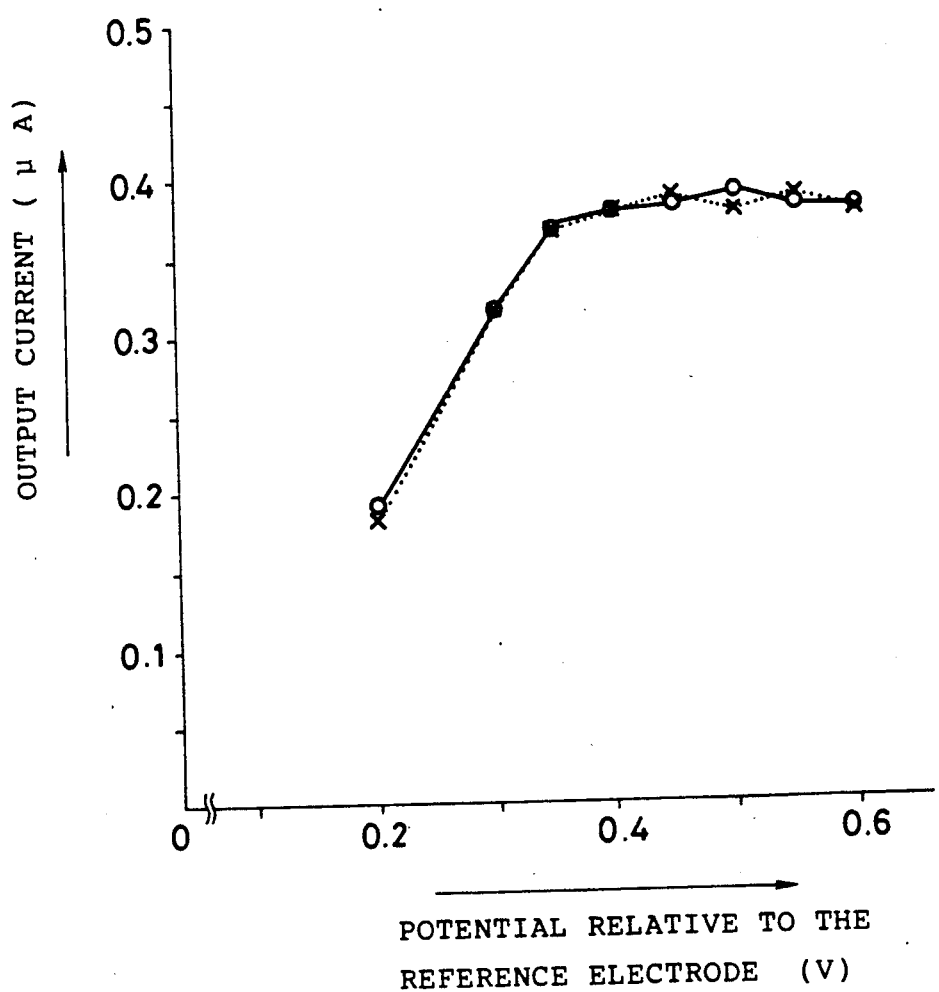
FIG. 6 is an electric current-voltage curve in relation to 1 mM hydrogen peroxide in Example 1 (in which "o" represents an initial value at the start of measurement, and "x" represents a value after measurement of 1000 samples)

The applied voltage was varied and it was confirmed that where 5 μl of an aqueous solution of 1 mM hydrogen peroxide was injected by a microsyringe from an injector 10, a distinct limiting current could be obtained (in FIG. 6, a generally constant current value is obtainable at a voltage between 0.35 V and 0.6 V).

Nextly, 5 μl of a sample including glucose or sucrose was introduced by a microsyringe through an injection port and measurement was carried out in the form of 3-electrode voltammetry by applying to the working electrode 5 a voltage of +0.60 V relative to the silver/silver chloride reference electrode, the working electrode 5 being employed as a hydrogen peroxide electrode. In this manner, measurement of samples including glucose or sucrose was continued for 30 days and a total of 1000 samples were analyzed (in FIG. 6, "o" denotes value at the start of use, "x" denotes value after measurement of 1000 samples).

Even after 30 days of measurement, it was confirmed that the limiting current could be detected with good reproducibility by using an aqueous solution of 1 mM hydrogen peroxide (FIG. 6 "x").

That is, even after measurement of 1000 samples containing glucose or sucrose, if a voltage of 0.35-0.6 V for the reference electrode is applied, there is no loss of response to glucose or sucrose. Therefore, even after 1000 samples measurements, stable measurement is possible.

Figure 7:
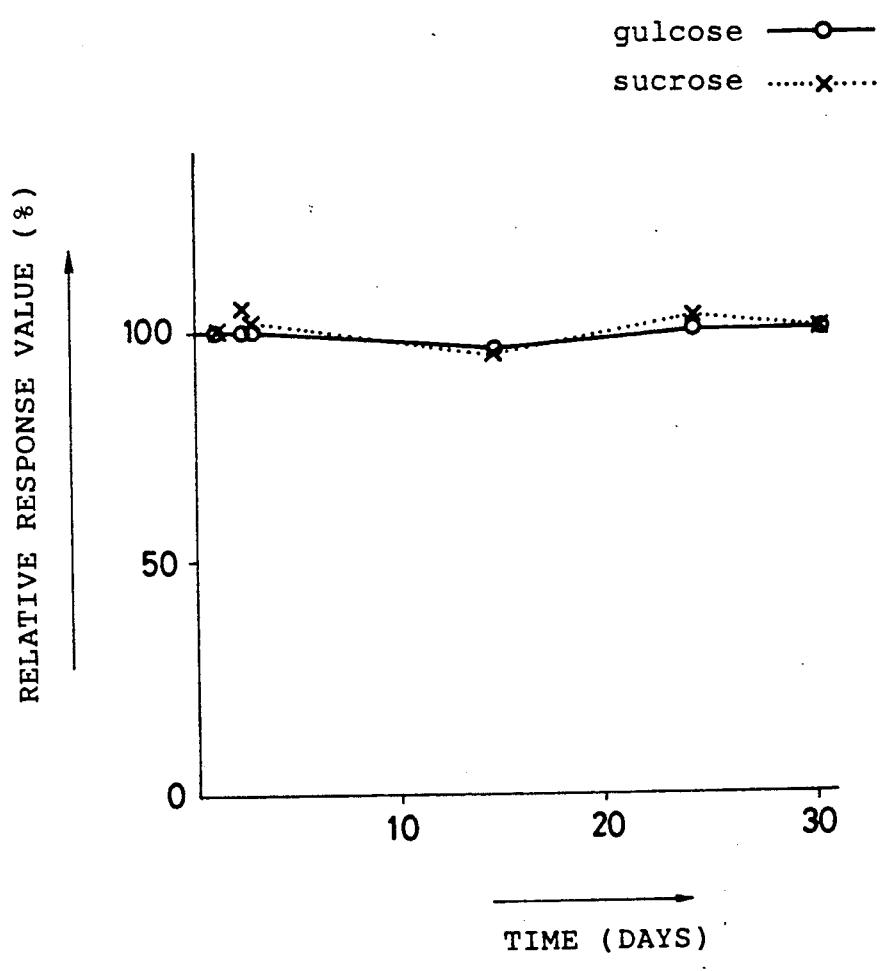
FIG. 7 is a graph showing changes with time in responses to glucose and sucrose in Example 1 (in which "o" represents response to glucose, and "x" represents response to sucrose)

During the 30 days of measurement, the enzyme electrode exhibited constant levels of response with respect to both glucose and sucrose, FIG. 7 indicates relative response values calculated on the basis of response current values at the start of measurement (in FIG. 7, "o" represent the values of glucose, "x" represent the values of sucrose).

COMPARATIVE EXAMPLE 1

Ends of a 2 mm dia., 10 mm long silver wire were finished flat with emery paper of 1600 mesh, and a 0.1 mm dia., 20 mm long silver lead wire was bonded to one end of the silver wire with a thermosetting conductive adhesive The assembly was heated for curing in an electric oven at 120° C. for one hour.

The outer periphery of the silver wire was covered with a heat shrinkable Teflon tube, and the front end portion of the so covered silver wire was immersed in a buffer solution of 0.1M sodium phosphate containing 0.05M potassium chloride at pH 7.0, which was employed as a working electrode, with a 1 cm square platinum electrode as a counter electrode and SCE as a reference electrode. Electrolysis was carried out at +0.2 V for 30 minutes at room temperature.

After the end of electrolysis, the silver wire was washed lightly in water, which was then fixed to an electrode supporting body. A plug type connector having a silver lead wire soldered thereto was mounted to the supporting body. Thus, a silver/silver chloride reference electrode was obtained.

Nextly, a working electrode having a immobilized enzyme membrane formed thereon was prepared in same way as in Example 1.

The silver/silver chloride reference electrode and the working electrode were mounted in the same measuring cell as was used in Example 1. A pipe connector having conductivity was disposed on a pipeline connected to the measuring cell, and at the downstream of the pipeline, which was employed as an auxiliary electrode or counter electrode. The measurement was carried out in the same manner as in Example 1.

Figure 8:
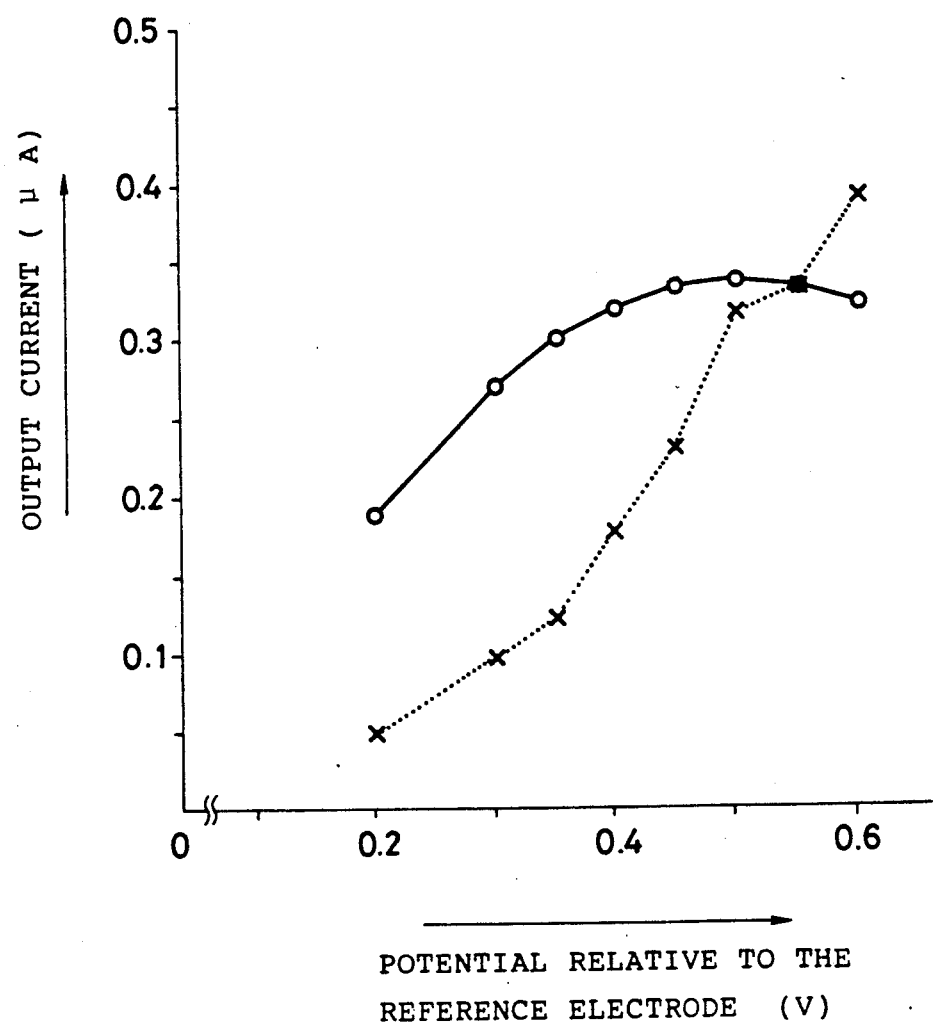
FIG. 8 is an electric current-voltage curve in relation to 1 mM hydrogen peroxide in Comparative Example 1 (in which "o" represents an initial value at the start of measurement, and "x" represents a value after measurement of 1000 samples)

As can be seen from FIG. 8, responses to hydrogen peroxide, after measurement of 1000 samples, became indistinct with respect to the position of detection for limiting current. FIG. 8 shows that after 1000 sample measurements, current value, unlike that at the start of measurement, varied with changes in potential, and therefore no stable measurement was possible (in FIG. 8, "o" denotes value at start of use and "x" denotes value after measurement of 1000 samples).

Figure 9:
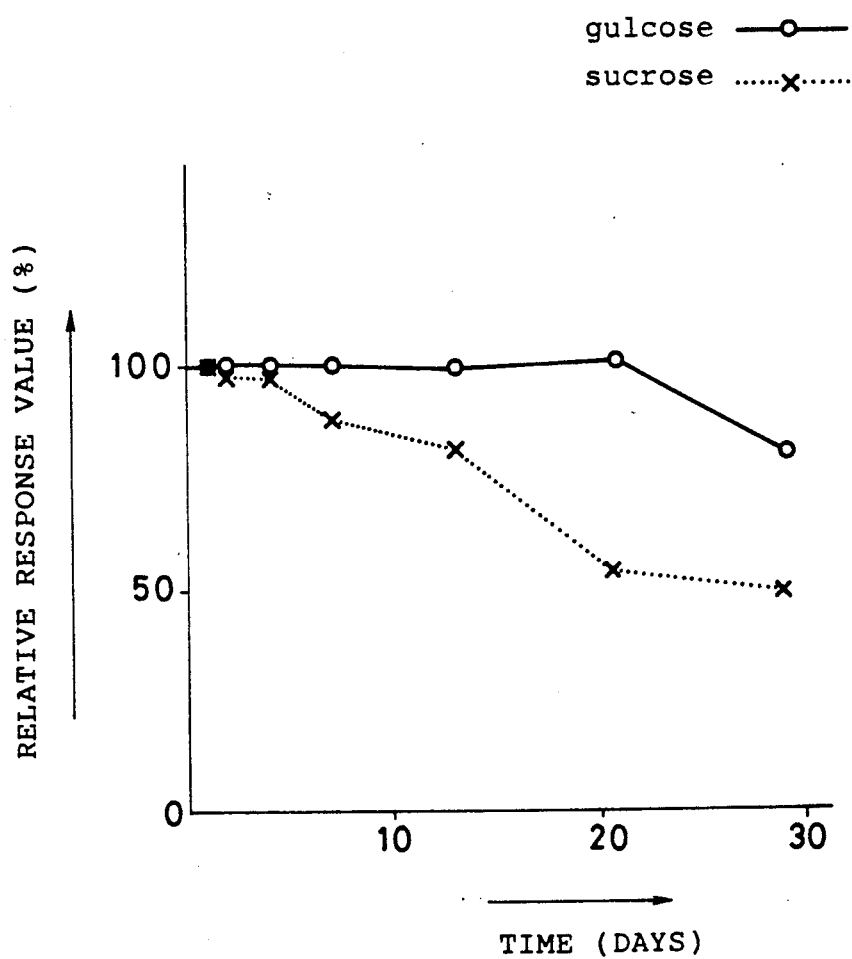
FIG. 9 is a graph showing changes with time in responses to glucose and sucrose in Comparative Example 1 (in which "o" represents response to glucose, and "x" represents response to sucrose)

Measurement of samples containing glucose or sucrose was continued for 30 days in the same manner as in Example 1, and a total of 1000 samples were analyzed. The results of the analysis indicated that the responses to glucose or sucrose were as shown in FIG. 9.

A peel of the silver chloride layer was witnessed at the upstream side location on the reference electrode, and it is found that the physical strength of the silver chloride containing layer is lowered. Therefore, a newly prepared silver/silver chloride reference electrode having no hydrophilic gel layer was mounted in position in same way as the previous one, and responses of the enzyme electrode were examined. Responses of same value as the initial response value were obtained with respect to glucose, the reason, that the relative response value is falling down, is the peels of the silver chloride containing layer. But responses to sucrose showed only a value level corresponding to about 40% of the relevant initial response value. The reason was that invertase was inactivated by silver ions flowed out of the reference electrode.

EXAMPLE 2

The same silver wire element as the one used in preparing the reference electrode in Example 1 was used and a reference electrode was produced. But when forming a silver chloride containing layer by the electroplating technique, 10 mg/ml of bovine serum albumin was dissolved in a buffer solution of 0.1M sodium phosphate at pH 7.0 containing 0.05M potassium chloride. Except above operation, in the same way as in Example 1, a silver wire was immersed in this buffer solution and electrolysis was carried out.

After the end of the electrolytic operation, a gel layer of bovine serum albumin was formed in the same manner as in Example 1. This electrode was employed for the same purpose of measurement as in Example 1. Satisfactory results were obtained. The results are similar to Example 1 as shown in FIGS. 6 and 7. More particularly, visual examination witnessed excellent bond between the hydrophilic gel layer and silver containing chloride layer, and accordingly the percentage of rejects during the process of manufacture was lowered.

EXAMPLE 3

To prepare the reference electrode 31 shown in FIG. 5, ends of a 2 mm dia. silver wire were finished flat with emery paper of 1600 mesh, and the outer periphery of the wire was covered with a heat shrinkable Teflon material. The front end portion of the silver wire was immersed in a buffer solution of 0.1M sodium phospate at pH of 7.0 containing 10 mg/ml of bovine serum albumin (Fraction V, produced by Sigma) and 0.05M potassium chloride, which was employed as a working electrode, with a 1 cm square platinum electrode as a counter electrode and SCE as a reference electrode. Electrolysis was carried out at +0.2 V for 30 minutes at room temperature. After the end of electrolysis, the silver electrode was washed lightly in water and then dipped in an aqueous solution of 1.0% glutaraldehyde for 5 minutes. Subsequently, for crosslinking and curing treatment of the silver chloride containing layer, the electrode was dried at 40° C. for 15 minutes.

The silver/silver chloride reference electrode thus prepared, as reference electrode 31, was mounted in the flow type measuring apparatus as shown in FIG. 5, so that the silver chloride containing layer formed thereon was in direct contact with the flow of the buffer solution.

Figure 10:
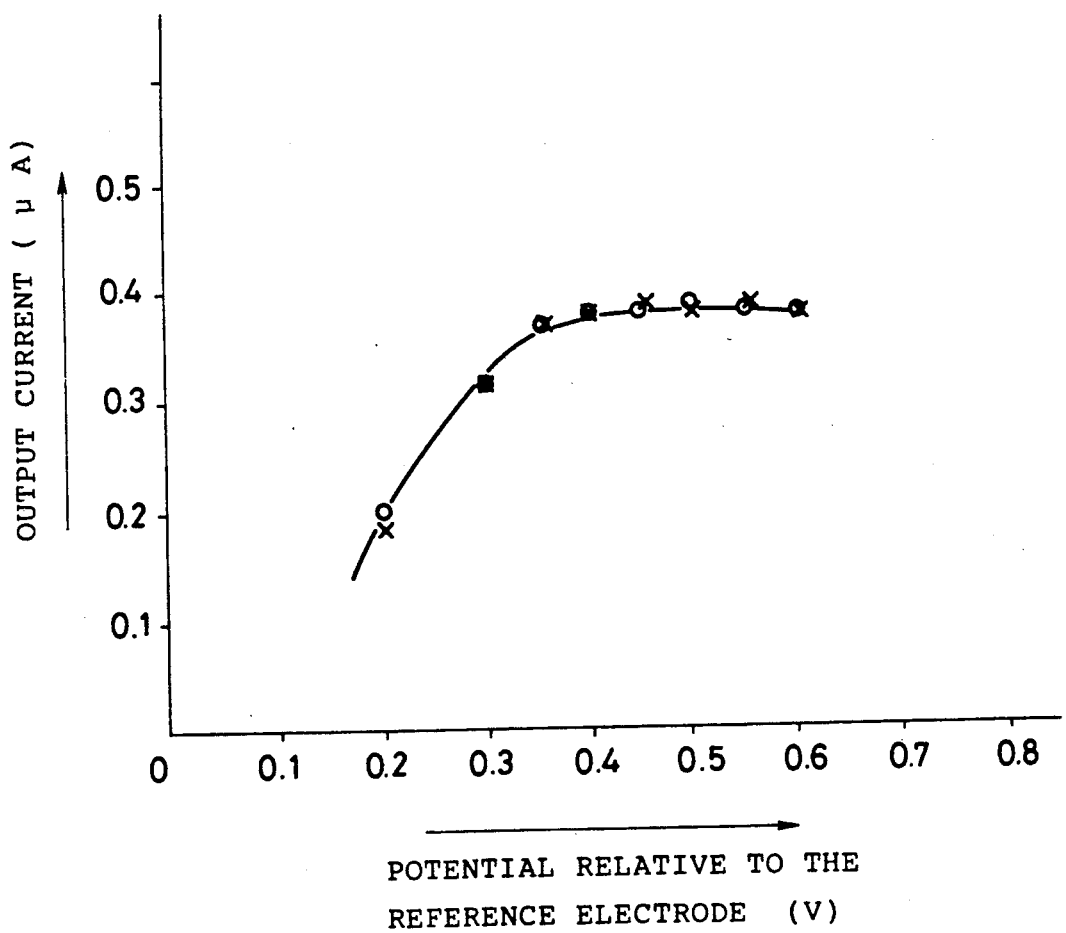
FIG. 10 is an electric current-voltage curve in relation to 1 mM hydrogen peroxide in Example 3 (in which "o" represents an initial value at the start of measurement, and "x" represents a value after measurement of 1500 samples)

A working electrode 33 of 2 mm diameter having both glucose oxidase and bovine serum albumin immobilized on the platinum wire with glutaraldehyde was mounted in a measuring cell 32 so that the working electrode was positioned at the opposite side of the reference electrode 31 relative to the flow path. A buffer solution of 0.1M sodium phosphate at pH 7.0 containing 0.05M potassium chloride was caused to flow at a flow rate of 1.0 ml/min by means of a pump 34. The following measurements were made in a thermostat 35 (inner temperature of 37.0±0.2° C.). Applied voltage was varied and it was confirmed that where 5 μl of an aqueous solution of 1 mM hydrogen peroxide was introduced, a distinct limiting current could be obtained. In FIG. 10, generally constant current value was obtained at a voltage between 0.35 V–0.7 V.

Nextly, 5 μl of a sample containing glucose was injected by a microsyringe from an injector 36, and a voltage of +0.45 V relative to the reference electrode was applied to the working electrode as a hydrogen peroxide electrode, whereby measurement in the form of 2-electrode voltammetry was carried out. In this manner, measurement of samples containing glucose was continued for 20 days, and a total of 1500 samples was analyzed.

Even after the 20-day measurement, it was confirmed that the limiting current could be detected with good reproducibility by using an aqueous solution of 1 mM hydrogen peroxide as shown in FIG. 10. That is, even after the measurement of 1500 samples, the predetermined current value could be obtained in the same way as at the start of measurement, when a voltage of 0.35–0.7 V for the reference electrode was applied. Therefore, the reference electrode of the invention permits constantly stable measurement (in FIG. 10, "o" denotes value at start of measurement and "x" denotes value after measurement of 1500 samples). Further, by visual examination of the silver/silver chloride reference electrode removed from the cell it was confirmed that there was no abnormality with respect to the surface of the reference electrode, such as peel of the silver chloride containing layer.

COMPARATIVE EXAMPLE 2

Figure 11:
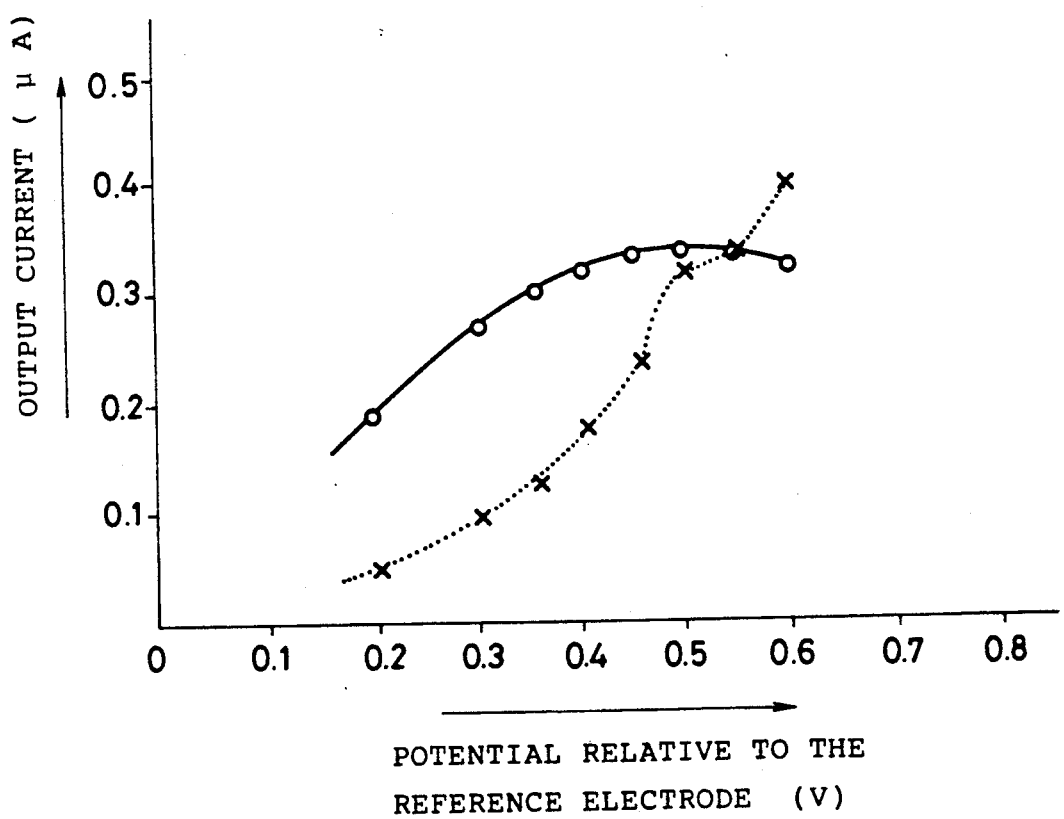
FIG. 11 is an electric current-voltage curve in relation to 1 mM hydrogen peroxide in Comparative Example 3 (in which "o" represents an initial value at the start of measurement, and "x" represents a value after measurement of 1500 samples).

A reference electrode was prepared in the same way as in Example 3 except that the electrolytic solution contained no bovine serum albumin and no curing treatment was employed That is, the silver wire was similarly electrolyzed in a buffer solution of 0.1M sodium phosphate at pH 7.0 containing 0.05M potassium chloride only. After the end of electrolysis, the silver wire was washed lightly in water and the reference electrode thus obtained was mounted in a flow type measuring apparatus as shown in FIG. 5, and measurement was carried out in the same way. The results of the measurement are shown in FIG. 11. Apparently, the position of limiting current detection was indistinct after measurement of 1500 samples. Unlike the value at start of measurement, current value varied along with the potential of the reference electrode after measurement of 1500 samples, which tells that no constantly stable measurement is possible with such reference electrode. (In FIG. 11, "o" denotes value at start of measurement and "x" denotes value after measurement of 1500 samples). Further, peels of the silver chloride containing layer were found on the surface of the reference electrode at several upstream side locations.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A silver/silver chloride reference electrode, comprising:
   a silver electrode portion;
   a first layer, containing a mixture of silver, silver chloride and protein, on said silver electrode portion, wherein said protein is crosslinked to crosslink said first layer, and wherein said first layer is formed by processing said silver electrode portion electrolytically in an electrolyte solution containing chloride ions and a protein having an isoelectric point lower than the pH of said electrolyte solution to form a thin layer and then treating said thin layer with a crosslinking agent to crosslink said protein to form said first layer; and
   a hydrophilic gel layer formed on said first layer such that said first layer can contact an electrolytic solution through said hydrophilic gel layer.

2. A silver/silver chloride reference electrode as claimed in claim 1, wherein said hydrophilic gel layer has a thickness of 0.1–20 mm.

3. A silver/silver chloride reference electrode as claimed in claim 1, wherein said hydrophilic gel layer is composed of at least one selected from the group consisting of polysaccharide gel, hydrophilic synthetic polymer gel and protein gel.

4. A silver/silver chloride reference electrode as claimed in claim 3, wherein said polysaccharide gel is composed of at least one selected from the group consisting of agarose, agaropectin and K-carrageenan.

5. A silver/silver chloride reference electrode as claimed in claim 3, wherein said hydrophilic synthetic polymer gel is composed of at least one selected from the group consisting of polyacrylamide and polyvinylalcohol.

6. A silver/silver chloride reference electrode as claimed in claim 3, wherein said protein gel is composed of (a) at least one selected from the group consisting of albumen, globulin and gelatin, and (b) a hydrophilic gel layer crosslinking agent for crosslinking the hydrophilic gel layer.

7. A silver/silver chloride reference electrode as claimed in claim 6, wherein said crosslinking agent is an aldehyde.

8. A silver/silver chloride reference electrode as claimed in claim 7, wherein said aldehyde is composed of at least one selected from the group consisting of formaldehyde, glutaraldehyde and glyoxal.

9. A silver/silver chloride reference electrode as claimed in claim 3, wherein said protein gel is composed of albumin and a crosslinking agent.

10. A silver/silver chloride reference electrode as claimed in claim 1, wherein said protein is composed of at least one selected from the group consisting of globulin, ovalbumin, serum albumin, collagen, and gelatin.

11. A silver/silver chloride reference electrode as claimed in claim 1, wherein said crosslinking agent is composed of at least one selected from the group consisting of formaldehyde, glutaraldehyde and glyoxal.

12. A silver/silver chloride reference electrode as claimed in claim 1, wherein said hydrophilic gel layer is composed of at least a protein and a crosslinking agent, and said crosslinking agent of said hydrophilic gel layer is the same as the crosslinking agent of said first layer.

13. A silver/silver chloride reference electrode formed by the steps of:
   providing an electrolytic solution containing chloride ions;
   dissolving protein having an isoelectric point lower than the pH of said electrolytic solution containing chloride ions in said electrolytic solution;
   processing a silver electrode electrolytically in said electrolytic solution to form a layer containing a mixture of silver, silver chloride and protein; and
   treating said formed layer with a crosslinking agent to crosslink the protein in the layer.

14. A measuring apparatus comprising:
   a silver/silver chloride reference electrode having a first layer containing silver chloride, and a hydrophilic gel layer formed on said first layer, whereby said first layer can contact an electrolytic solution through said hydrophilic gel layer and wherein said first layer is formed by processing a silver electrode electrolytically in an electrolyte solution containing chloride ions and a protein having an isoelectric point lower than the pH of said electrolytic solution, whereby a layer is formed containing a mixture of silver, silver chloride and protein, and then treating the formed layer with a crosslinking agent to crosslink the protein; and
   an immobilized enzyme working electrode.

15. A measuring apparatus as claimed in claim 14, wherein said immobilized enzyme working electrode comprises an immobilized enzyme which has the characteristic that its activity is inhibited by silver ions.

16. A measuring apparatus as claimed in claim 15, wherein at least one of said enzyme is selected from the group consisting of L - sorbose oxidase, inulinase, $\alpha$ - D - glucosidase, $\beta$ - D - glucosidase, $\beta$ - D - galactosidase, invertase and glucoamylase.

17. A measuring apparatus as claimed in claim 14, and further comprising a measuring cell having a flow path and means for holding the silver/silver chloride reference electrode and the immobilized working electrode facing said flow path.

* * * * *